United States Patent
Cattani

[19]

[11] Patent Number: 6,022,216
[45] Date of Patent: Feb. 8, 2000

[54] FLUID SEPARATOR FOR DENTAL ASPIRATION APPARATUS

[75] Inventor: Ennio Cattani, Parma, Italy

[73] Assignee: Cattani S.p.A., Parma, Italy

[21] Appl. No.: 09/298,166

[22] Filed: Apr. 23, 1999

[30] Foreign Application Priority Data

May 29, 1998 [IT] Italy .............................. MO98A0119

[51] Int. Cl.[7] .................................................. A61C 17/06
[52] U.S. Cl. ............................................................ 433/92
[58] Field of Search ............................ 433/92; 210/754, 210/755, 764, 749

[56] References Cited

U.S. PATENT DOCUMENTS

| | | | |
|---|---|---|---|
| 4,245,989 | 1/1981 | Folkenroth et al. | 433/92 |
| 4,564,374 | 1/1986 | Hofmann | 433/92 |
| 5,205,743 | 4/1993 | Ludvigsson et al. | 433/92 |
| 5,741,397 | 4/1998 | Kraver | 433/92 X |
| 5,788,852 | 4/1998 | Mescon | 433/92 X |

*Primary Examiner*—Nicholas D. Lucchesi
*Attorney, Agent, or Firm*—Browdy and Neimark

[57] ABSTRACT

A separator for dental aspiration apparatus comprises a drainage pump and a suction pump activated by two respective electric motors. Fluid coming from a patient's mouth during an operation comprises a liquid part and a gaseous part which must be separated from the liquid part before the liquid part is discharged. The fluid to be separated is introduced into the drainage pump. The liquid part is discharged through an outlet of the drainage pump, while the gaseous part is aspirated back by the suction pump and then evacuated through an outlet. A control and command unit comprises a timer, of known type, which is able to command start-up of the motor of the suction pump after a predetermined time lapse after startup of the motor of the drainage pump.

6 Claims, 1 Drawing Sheet

FLUID SEPARATOR FOR DENTAL ASPIRATION APPARATUS

BACKGROUND OF THE INVENTION

The prior art in this field teaches dental apparatus which remove fluids from a patient's mouth during an operation. These fluids comprise a gaseous part and a liquid part. The gaseous part is generally air, while the liquid part is usually composed of water, organic liquids and other liquids used in dental apparatus. The gaseous part has to be separated from the liquid part before the latter is purified and ultimately discharged into the sewers. The prior art teaches separators for this purpose, which combine the action of a centrifuge drainage pump with that of a suction pump. In these separators the fluids which are to be separated are sent into the centrifuge pump; the suction pump creates a depression inside the centrifuge pump causing the gaseous part of the fluid to be aspirated by the suction pump, while the liquid part exits through an aperture afforded in the centrifuge pump. The prior art teaches separators, for example in European Publications EP 0 237 708 and EP 0 766 008, in which a single motor is used to drive both the centrifugal and the suction pumps.

In these known separators, however, the suction pump might aspirate some of the liquid, especially when the separator is started up. This happens mainly because at the moment when the separator is stopped, the liquid remaining in the tubes of the separator itself might flow towards the drainage pump and collect in the bottom thereof, eventually reaching a certain level so that when the separator is started up again a part of the liquid can be sucked up by the suction pump. This both damages the suction pump and may cause dispersion of tiny droplets of a pollutant which is expelled from the suction pump and thus constitutes an environmental risk.

SUMMARY OF THE INVENTION

The main aim of the present invention is to obviate the above-mentioned drawback by providing a separator which is able to guarantee against the risk of undesired liquid aspiration on the part of the air suction pump.

An advantage of the present invention is that it prevents random and uncontrolled dispersion of droplets of pollutant liquid at all separator operating phases, especially at start-up and shut-down of the pump itself.

A further advantage of the invention is that it provides a separator highly unsusceptible to flooding due to bad drainage pump operation.

These aims and advantages and more besides are all attained by the present invention, as it is characterised in the appended claims.

BRIEF DESCRIPTION OF THE DRAWINGS

Further characteristics and advantages of the present invention will better emerge from the detailed description that follows of a preferred but non-exclusive embodiment of the invention, illustrated purely by way of a non-limiting example in the accompanying figure of the drawing, in which.

DESCRIPTION OF THE PREFERRED EMBODIMENTS

Figure 1:
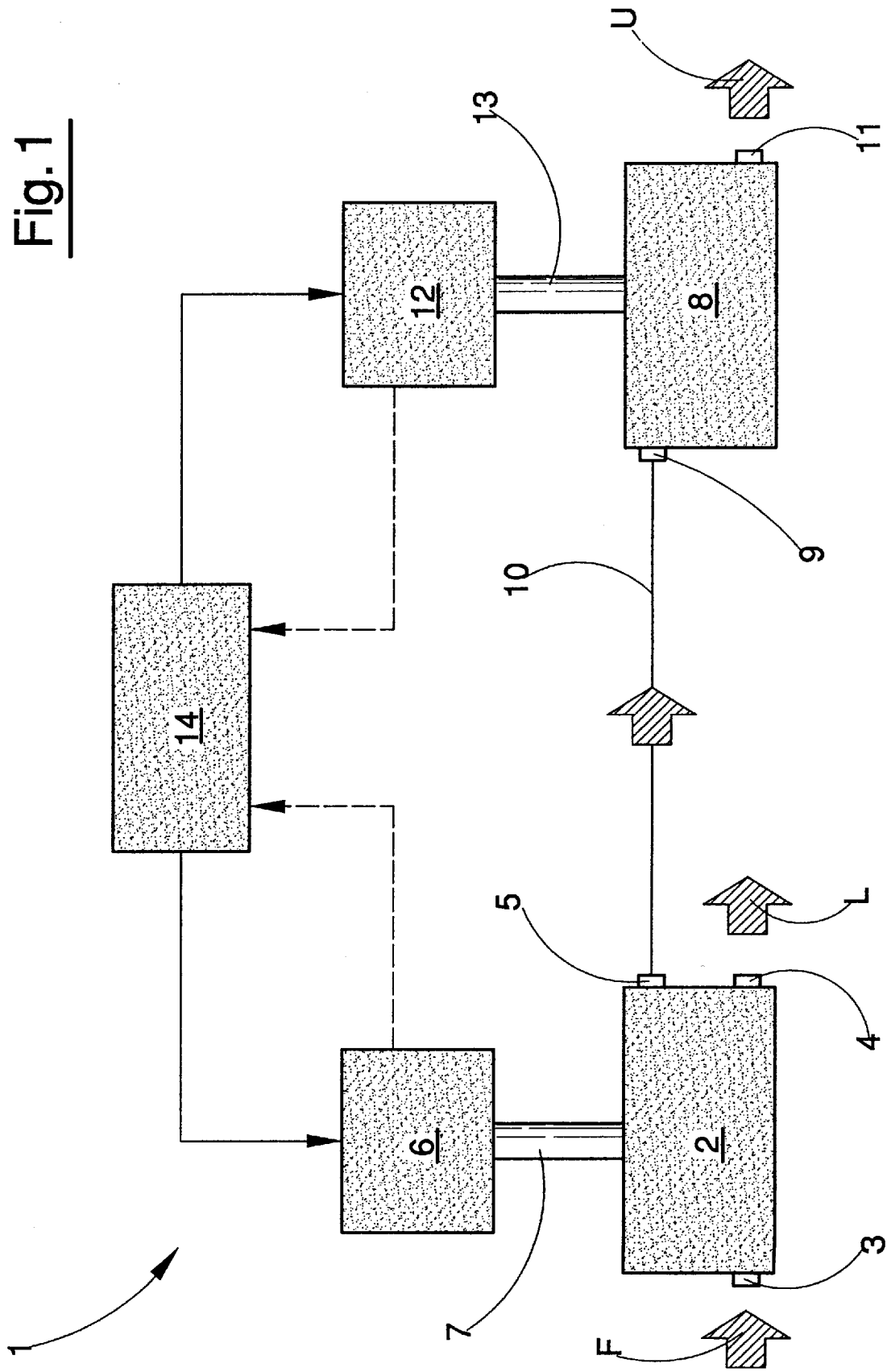
FIG. 1 is a diagram of a separator made according to the invention.

With reference to the figure, 1 denotes in its entirety a separator for dental aspiration apparatus. The separator 1 comprises a centrifuge drainage pump 2 provided with a hole 3 for inlet of the fluid to be separated. The fluid enters the centrifuge pump 2 in the direction indicated by the arrow F of FIG. 1. The drainage pump 2 is further provided with an outlet hole 4 for the liquids exiting from the drainage pump 2 in the direction indicated by the arrow L of FIG. 1, to be sent on to discharge into the drains. The drainage pump 2 also exhibits an air outlet hole 5. The drainage pump 2 is actuated by a first electric motor 6, having a drive shaft 7 coaxially bearing the drainage pump 2 impeller. The separator 7 comprises a suction pump 8, predisposed for extraction of gases from the fluid introduced into the separator 1, which suction pump 8 is provided with a hole 9 for inlet of the air, which hole 9 is connected, through a conduit represented schematically in FIG. 1 and denoted by 10, with the outlet hole 5 of the drainage pump 2.

The suction pump 8 is further provided with an outlet hole 11 for the air, through which the aspirated air is evacuated in the direction indicated by the arrow U in FIG. 1. The separator 1 also comprises a second motor 12, distinct from the first motor 6, which sets the suction pump 8 impeller in rotation by means of a shaft 13. Thus each motor 6 and 12 sets a respective pump 2 and 8 in rotation.

The separator 1 is provided with a central control unit 14, connected to the two motors 6 and 12, which controls and regulates the operation of the separator 1 itself. The control unit 14 is equipped with a first timer, of known type, which is predisposed to command start-up of the motor 12 of the suction pump 8 after a predetermined time lapse following the start-up of the motor 6 of the drainage pump 2. This delay in suction pump 8 start-up with respect to drainage pump 2 start-up can be, for example, in the order of a couple of seconds. Preferably the delay can be regulated.

The control unit 14 comprises a second timer, of known type, able to control the shut-down of the drainage pump 2 motor 6 after a predetermined time following the shut-down of the suction pump 8 motor 12. This delay in drainage pump 8 shut-down might be, for example, of the order of a few seconds, and can be regulated. It is further possible, given that the drainage pump 8 can be located in a different place to the workplace, and that, in any case, the pump runs very quietly, for the delay time to be in the order of a few minutes. This means that, especially with plants having long tubes, the greater part of the liquid collected in the tubes themselves can be evacuated.

The control unit 14 is further provided with a sensor, of known type, for detecting a drainage-pump shut-down situation. The sensor can also provide a command signal which, when motor 6 shut-down is detected, stops the motor 12 of the suction pump 8. In this particular example the sensor detects the current supply to the motor 6 of the drainage pump 2.

During operation, when the control unit 14 receives an external command to shut-down the separator 1, first it stops the suction pump 8 motor 12 and then, after a time lapse which can be regulated by adjusting the second timer, the drainage pump 2 motor 6. Thus the risk of having residual liquid accumulated (usually by force of gravity) in the separator 1 or in the apparatus tubes is reduced.

When, after a break in separator 1 operation, the control unit 14 receives an external re-start command, first the drainage pump 2 is actuated and only after, and after a regulated time lapse, is the suction pump 8 also started up. There is therefore a relatively short period of time in which only the drainage pump 2 is operating. This time period must be sufficient to enable the drainage pump 2 to evacuate, through the outlet 4, any liquid which during the previous break in operation may have collected by dripping in the bottom of the separator 1. If, for any reason, the motor 6 of the drainage pump 2 should stop, the control unit 14 immediately stops the suction motor 12, thus preventing flooding.

The separator 1 has the further advantage of being made in two distinct blocks, which can be variously positioned, giving a considerable degree of user freedom in choice of separator location.

What is claimed:

1. A separator for dental aspiration apparatus, comprising:

a drainage pump, provided with an inlet for a fluid to be separated; a first outlet for liquids and a second outlet for gases;

a suction pump, provided with an inlet for gases, which inlet is connected with said second outlet of the drainage pump;

two electric motors, each of which sets an impeller of a pump in rotation;

a first timer, for commanding start-up of one of said two electric motors, which drives the suction pump, after a predetermined time lapse has passed after start-up of another of said two electric motors, which drives the drainage pump.

2. The separator of claim 1, comprising a second timer, for commanding a shutdown of the electric motor driving the drainage pump after a predetermined time lapse from shutdown of the electric motor driving the suction pump.

3. The separator of claim 2, comprising a sensor, able to detect a shutdown situation of the electric motor driving the drainage pump and also able to send a shutdown command signal to the electric motor driving the suction pump.

4. The separator of claim 3, wherein the sensor is predisposed to detect the current supply of motor of the drainage pump.

5. The separator of claim 1, comprising a sensor, able to detect a shutdown situation of the electric motor driving the drainage pump and also able to send a shutdown command signal to the electric motor driving the suction pump.

6. The separator of claim 5, wherein the sensor is predisposed to detect the current supply of motor of the drainage pump.

* * * * *